United States Patent [19]
Basile et al.

[11] Patent Number: 5,628,970
[45] Date of Patent: May 13, 1997

[54] STERILIZATION TRAY ASSEMBLY COMPOSED OF A MINERAL FILLED POLYPROPYLENE

[75] Inventors: Mark Basile, Grosse Pointe; Steven Basile, Grosse Pointe Woods, both of Mich.

[73] Assignee: Healthmark Industries, Co., St. Clair Shores, Mich.

[21] Appl. No.: 534,194

[22] Filed: Sep. 26, 1995

[51] Int. Cl.⁶ .............................. A61L 2/06; A61L 2/20
[52] U.S. Cl. .................... 422/297; 422/300; 206/363
[58] Field of Search ............................ 422/297, 300, 422/292; 206/363, 439

[56] References Cited

U.S. PATENT DOCUMENTS

| | | | |
|---|---|---|---|
| 4,617,128 | 10/1986 | Nichols | 422/310 |
| 4,716,025 | 12/1987 | Nichols | 422/310 |
| 4,752,453 | 6/1988 | Nichols | 422/300 |
| 4,900,519 | 2/1990 | Nichols | 422/292 |
| 4,983,647 | 1/1991 | Ueno et al. | 523/220 |
| 5,080,874 | 1/1992 | Nichols | 422/300 |
| 5,165,539 | 11/1992 | Weber et al. | 206/363 |
| 5,183,643 | 2/1993 | Nichols | 422/297 |
| 5,202,098 | 4/1993 | Nichols | 422/300 |
| 5,271,892 | 12/1993 | Hanson et al. | 422/25 |
| 5,286,776 | 2/1994 | Ichikawa et al. | 524/449 |
| 5,397,239 | 3/1995 | Zaderej et al. | 439/55 |

*Primary Examiner*—Robert J. Warden
*Assistant Examiner*—E. Leigh Dawson
*Attorney, Agent, or Firm*—Brooks & Kushman P.C.

[57] ABSTRACT

The present invention is directed to a sterilization tray assembly for sterilizing medical instruments. The sterilization tray preferably includes a base tray and a cover. Also, a secondary tray may be mounted within the base tray. These components ideally include ventilation apertures to allow steam or vapor to pass through the sterilization tray assembly to effect sterilization of medical instruments stored therein. The components of the sterilization tray assembly preferably are made of a mineral filled polypropylene and most preferably is a homopolymer which is filled with calcium carbonate, 40% by weight. This material exhibits good heat deflection characteristics at high temperature while being relative inert to absorption of $H_2O_2$ vapor.

17 Claims, 3 Drawing Sheets

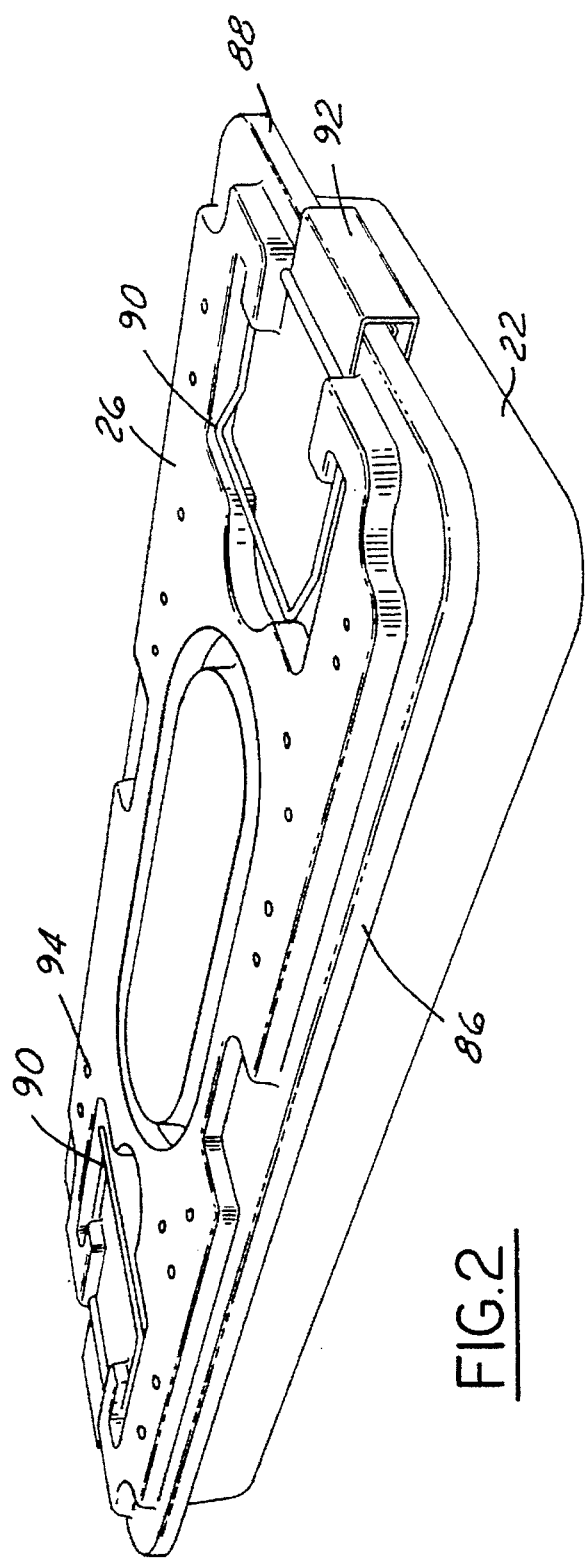
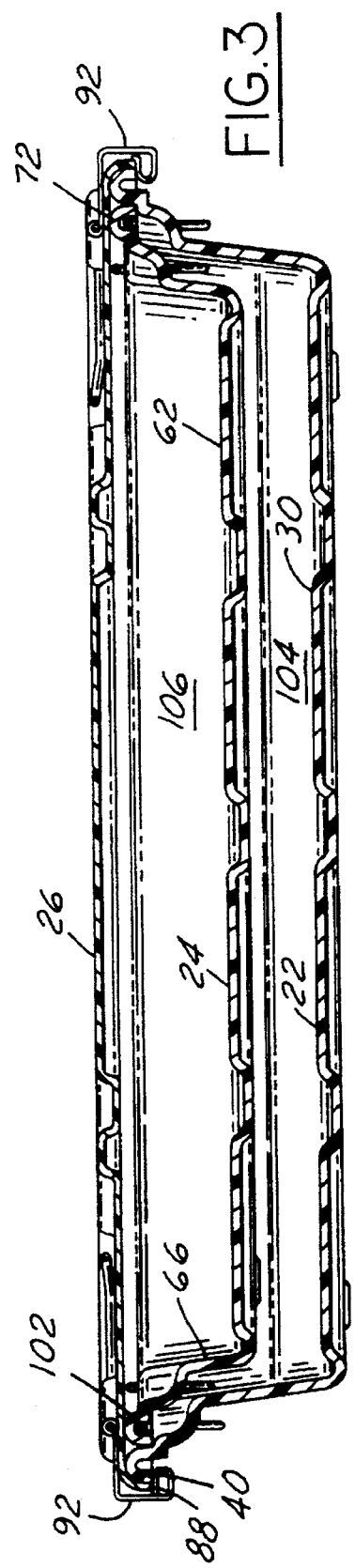

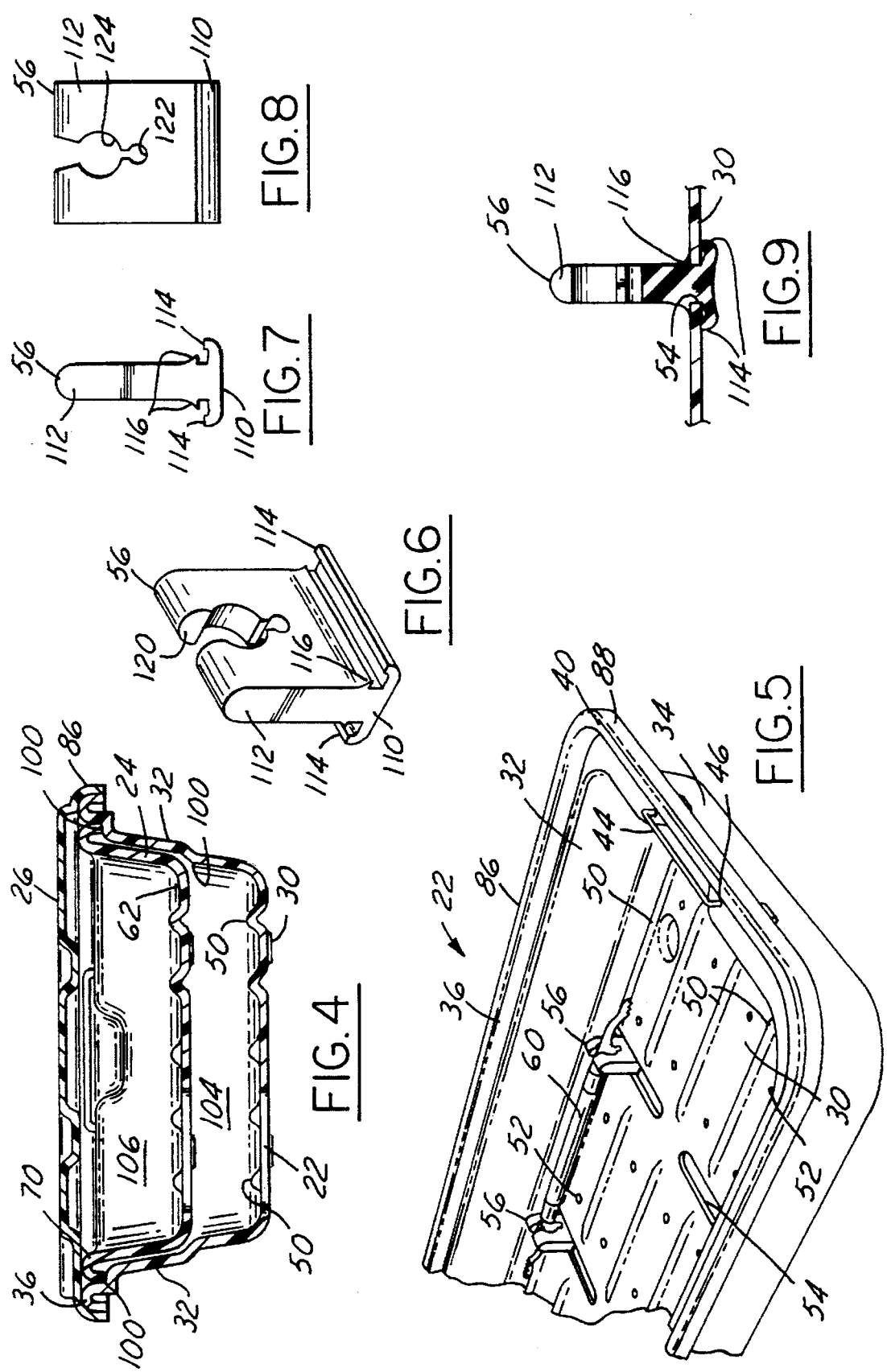

STERILIZATION TRAY ASSEMBLY COMPOSED OF A MINERAL FILLED POLYPROPYLENE

TECHNICAL FIELD

The present invention relates to sterilization trays, and more particularly, to sterilization trays which are made of molded plastic.

BACKGROUND OF THE INVENTION

Four basic methods have been used in the past to sterilize medical instruments which are retained within sterilization trays during sterilization operations. These methods include using (1) ethylene oxide (EO); (2) chemical soaking; (3) steam sterilization; and (4) plasma sterilization employing a hydrogen peroxide ($H_2O_2$) vapor.

The sterilization method using the ethylene oxide includes using a highly flammable and toxic gas which therefore require special precaution. Further, this sterilization technique requires a long time to complete. Thus, expensive medical instruments cannot be rapidly sterilized and used many times in a day. An advantage this method has over others is that sterilization occurs at a low temperature. However, overall this particular technique is expensive and is in disfavor.

The second method utilizes chemical soaking to sterilize instruments. This sterilization method can occur at low temperatures. However, the soaking generally takes a long time and therefore is undesirable. Further, the chemicals used to do the sterilization are often considered to be hazardous and require special handling and disposal.

The third method is steam sterilization. Instruments are placed within a sterilization tray and loaded into a sterilization device such as an autoclave. Using a combination of steam, time, temperature and pressure, the instruments in the autoclave are sterilized. An advantage to this particular method is that it is fast and cheap. However, the requirement of high temperature requires that sterilization trays be stable when placed in a high temperature environment for an extended period of time. That is, the sterilization tray should have a high heat deflection value, i.e., little deformation and dimensional change due to the extended heating.

Metal sterilization trays are quite good at retaining their shapes during high temperature sterilization. However, as many medical instruments are made of metal and are extremely expensive, the instruments are susceptible to being accidentally banged or scraped against the metal sterilization trays, thus damaging the medical instruments. Therefore, it is preferable that plastic sterilization trays be used. Currently, the plastic of choice for sterilization trays used in steam sterilization is Radel 5000. The Radel 5000 provides the desired heat deflection characteristics during extended high temperature sterilization cycles. Unfortunately, Radel 5000 is a relatively expensive material.

The newest of the above sterilization techniques is using a plasma which employs hydrogen peroxide ($H_2O_2$) as the sterilization agent. The advantage this particular method offers is that sterilization can occur at a relatively low temperature and with a relatively short time cycle. The short time cycle is important in the event that expensive instruments are to be used several times in a day. Unfortunately, sterilization trays made out of the Radel 5000 readily absorb the hydrogen peroxide. This absorption is undesirable because it often causes the machinery used in the plasma sterilization to shut down. Further, the absorbed hydrogen peroxide may later release from the sterilization trays and into the medical instruments or atmosphere which is undesirable.

Sterilization trays made of plastics other than Radel 5000 have been made for use in hydrogen peroxide plasma sterilization devices. However, these sterilization trays typically do not have sufficient heat deflection values to adequately withstand the temperatures of steam sterilization.

The present invention intends to overcome many of the shortcomings of the above described conventional sterilization trays.

SUMMARY OF THE INVENTION

It is an object of the present invention to provide a sterilization tray assembly which is relatively inert and non-absorbent to hydrogen peroxide vapor.

Another object of the present invention is to provide a sterilization tray which has a high heat deflection value while being considerable cheaper to make than conventional plastic sterilization trays having high heat deflection values.

The present invention includes a sterilization tray assembly. The assembly includes a base tray having a floor and a generally peripherally extending wall, preferably rectangular in configuration. The base tray is made of a mineral filled polypropylene containing 20%–50% of mineral filler based on the weight of the mineral filled polypropylene.

The mineral is ideally chosen from a group comprising calcium carbonate, clays and silicates. More preferably, the polypropylene is a homopolymer and the mineral filled polypropylene contains 30–35% mineral filler by weight, and most preferably is 40% by weight of calcium carbonate.

A cover, also made of the mineral filled polypropylene, is ideally included in the assembly. Also, an intermediate secondary tray may also be used. The resulting sterilization tray assembly has a relative high heat deflection value which is generally $H_2O_2$ non-absorbent and is relatively inexpensive to make.

BRIEF DESCRIPTION OF THE DRAWINGS

FIG. 2 is a perspective view of the sterilization tray assembly nested together;

FIG. 3 is a longitudinal sectional view of the sterilization tray assembly;

FIG. 4 is a transverse sectional view;

FIG. 5 is a fragmentary perspective view of the lower tray including retaining clips which hold an instrument to be sterilized;

FIG. 6 is a perspective view of one of the retaining clips;

FIG. 7 is an end view of the retaining clip;

FIG. 8 is front view of the retaining clip; and

FIG. 9 is a side sectional view of the retaining clip being held within a slot in the base tray.

BEST MODE FOR CARRYING OUT THE INVENTION

Figure 1:
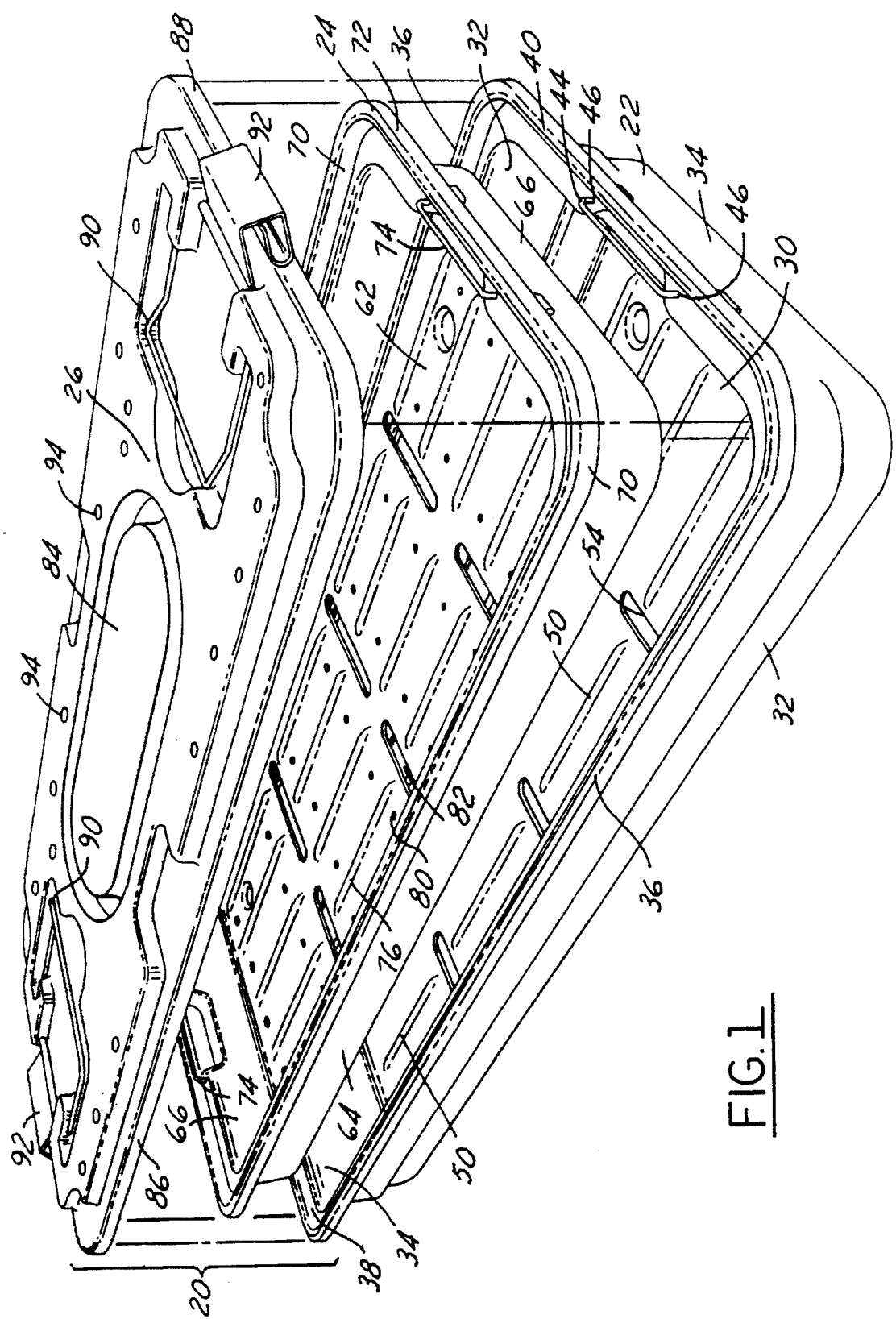
FIG. 1 is an exploded perspective view of a sterilization tray assembly, made in accordance with the present, comprising a base tray, a secondary tray and a cover.

FIG. 1 shows a sterilization tray assembly 20 made in accordance with the present invention. Sterilization tray 20 comprises a base tray 22, a secondary tray 24 and a cover 26.

Base tray 22 includes a floor 30 connected to a pair of transversely spaced longitudinal walls 32 and a pair of longitudinally spaced transverse walls 34. Extending across the tops of longitudinal walls 32 and transverse walls 34 are respective longitudinal lips 36 and transverse lips 40. Each of lips 36 and 40 curl or roll outwardly. A pair of handles 44 are attached to handle apertures 46 formed in respective transverse lips 40.

Floor 30 has a plurality of parallel rows of longitudinally extending upstanding ribs 50 which extend upwardly from the rest of floor 30. Spaced between ribs 50 are numerous ventilation apertures 52. Also formed in floor 30 are a series of transversely extending slots 54. As best seen in FIG. 5, retaining clips 56 can be inserted into slots 54. Retaining clips 56 serve to hold medical instruments 60 which are to be sterilized. Retaining clips 56 will be further described later.

Secondary tray 24 also has a floor 62 and a pair of longitudinal walls 64 and a pair of transverse walls 66. Longitudinal lips 70 and transverse lips 72 are formed atop longitudinal walls 64 and transverse walls 66 in manner similar to the formation of base tray 22. Again, lips 70 and 72 are rolled or curled outwardly. Longitudinally spaced handles 74 are attached to lips 72 to allow secondary tray 24 to be lifted from base tray 22. Floor 62, like floor 30, has numerous ventilation apertures 80 and elongate slots 82 which are capable of holding retaining clips 56.

Cover 26 has a main body 84 with numerous depressions formed therein and downwardly depending longitudinal flanges 86 and transverse flanges 88. Pivotally mounted to the top of body 84 at either longitudinal end are handles 90. Body 84 has numerous ventilation apertures 94 spaced therethroughout. C-shaped retaining clamps 92 are pivotally mounted to either end of body 84.

Looking now to FIG. 4, longitudinal walls 32 have respective steps 100 formed therein adjacent longitudinal lips 36. Similarly, transverse walls 34 also have transverse steps 102 as best seen in FIG. 3. Longitudinal and transverse lips 70 and 72 of secondary tray 24 rest upon steps 100 and 102. Cover 26 sits upon secondary tray 24 with flanges 86 and 88 fitting over lips 36 and 40 of base tray 22. Clamps 92 can be snapped over transverse lips 40 to secure cover 26 to base tray 22 with secondary tray 24 being captured therebetween. Sterilization chambers 104 and 106 are created between base tray 22 and secondary tray 24 and between secondary tray 24 and cover 26.

A retaining clip 56 is shown FIGS. 5–9. Retaining clip 56 has a base portion 110 and an upstanding stem portion 112. Base portion 110 has outwardly flaring and curled flanges 114. Stem portion 112 has a pair of retaining ribs 116 near base portion 110. A slot 120 is formed in the upper portion of stem portion 112 which includes a small hole 122 and a larger hole 124. As shown in FIG. 5, a pair of the retaining clips 56 can be used to mount a medical instrument 60. FIG. 9 illustrates that stem portion 112 can be inserted through a slot 54 in floor 30 with ribs 116 cooperating with flanges 114 to clampingly secure retaining clip 56 to base tray 22. As alternative to using retaining clips 56, a conventional elastomeric mat may be placed upon floor 30 to hold instruments during sterilization.

Each of base tray 22, secondary tray 24 and cover 26 are ideally made of a mineral filled polypropylene. This preferred material is sold by Ferro Specialty Plastics Group of Evansville, Indiana under the product name DPP40WA-ZZ. Most preferably, the polypropylene is a homopolymer and the mineral is calcium carbonate. However, copolymers of ethylene and propylene with ethylene contents up to about 3.5 weight percent are also suitable. Other mineral fillers may also be used, as for example talc, kaolin, bentonite, wollastonite, and other naturally occurring clay minerals, silicates, and the like. The range of mineral filler, by weight, is from 20 to 50%, ideally between 30–45% and most preferably, is 40%. The mineral filled polypropylene should have a heat deflection temperature as measured by ASTM D-648 of 130° C. or higher. The mineral filled polymer has proven to provide excellent heat deflection characteristics at a relatively low cost while being generally inert to hydrogen peroxide vapor absorption. Preferably, the floors and walls of base tray 22, secondary tray 24 and cover 26 each have a starting wall thickness of at least 0.185 inch prior to molding and a thickness of 0.150 inch after molding is complete.

While in the foregoing specification this invention has been described in relation to a certain preferred embodiment thereof, and many details have been set forth for the purpose of illustration, it will be apparent to those skilled in the art that the invention is susceptible to alteration and that certain other details described herein can vary considerably without departing from the basic principles of the invention.

What is claimed is:

1. A sterilization tray assembly comprising:
a base tray having a floor and a peripherally extending wall, one of the floor and the wall having ventilation apertures therein;
wherein the base tray is made of polypropylene containing from 20% to 50% of a filler based on the weight of the filled polypropylene, said filler consisting essentially of a mineral filler.

2. The sterilization tray assembly of claim 1 wherein:
the mineral is chosen from a group comprising calcium carbonate, clays, and silicates.

3. The sterilization tray assembly of claim 2 wherein:
the mineral is calcium carbonate.

4. The sterilization tray assembly of claim 1 wherein:
the mineral filled polypropylene contains 30–45% mineral by weight.

5. The sterilization tray assembly of claim 4 wherein:
the mineral is calcium carbonate.

6. The sterilization tray assembly of claim 5 wherein:
the mineral filled polypropylene is approximately 40% calcium carbonate by weight.

7. The sterilization tray assembly of claim 1 wherein:
the polypropylene is a homopolymer.

8. The sterilization tray assembly of claim 1 further comprising:
a cover made of a mineral filled polypropylene.

9. The sterilization tray assembly of claim 8 wherein:
the mineral is calcium carbonate.

10. The sterilization tray assembly of claim 8 wherein:
the polypropylene is filled containing 20%–50% of a filler based on the weight of the filled polypropylene, said filler consisting essentially of a mineral filler.

11. The sterilization tray assembly of claim 8 wherein:
the polypropylene is filled containing 30%–45% of mineral filler based on the weight of the mineral filled polypropylene.

12. The sterilization tray assembly of claim 1 wherein:
the polypropylene is propylene homopolymer containing about 40% by weight mineral filler and having a heat deflection temperature as measured by ASTM D-648 of about 130° C. or higher.

13. The sterilization tray assembly of claim 1 wherein:
the base tray has a plurality of through apertures therein.

14. The sterilization tray assembly of claim 1 further comprising:

a cover which fits over the base tray.

15. The sterilization tray assembly of claim 14 wherein:

the cover includes a plurality of through apertures therein.

16. The sterilization tray assembly of claim 15 further comprising:

a secondary tray disposed between the cover and the base tray.

17. The sterilization tray assembly of claim 16 wherein:

the secondary tray has a plurality of through apertures therein.

* * * * *